United States Patent
Winkelman et al.

[19]

[11] Patent Number: 6,132,353
[45] Date of Patent: Oct. 17, 2000

[54] APPARATUS AND METHOD FOR SEPARATING PLASMA OR SERUM FROM THE RED CELLS OF A BLOOD SAMPLE

[76] Inventors: James W. Winkelman, 62 Rangeley Rd., Brookline, Mass. 02167; Oren Zinder, Hiamhazzad Street, #3, Haifa, Israel, 31071; Manfred Grumberg, 64 Dania Street, Haifa, Israel, 34980; Jacob Schreibman, 45 Azmon Street, Alfey-Menashe, Israel, 44851

[21] Appl. No.: 08/897,420

[22] Filed: Jul. 21, 1997

Related U.S. Application Data

[63] Continuation-in-part of application No. 08/734,235, Oct. 21, 1996, abandoned.

[51] Int. Cl.⁷ .................................................. B04B 5/02
[52] U.S. Cl. ................................. 494/16; 494/37; 494/47; 494/85
[58] Field of Search ................................. 494/16, 20, 31, 494/33, 34, 37, 38, 43, 47, 85; 210/416.1; 422/72

[56] References Cited

U.S. PATENT DOCUMENTS

| | | |
|---|---|---|
| 1,718,593 | 6/1929 | Smith . |
| 1,928,998 | 10/1933 | Kovacs . |
| 3,190,547 | 6/1965 | Shanley et al. . |
| 3,494,508 | 2/1970 | Hoefer . |
| 3,586,064 | 6/1971 | Brown et al. . |
| 3,648,927 | 3/1972 | Abbe et al. ................................. 494/43 |
| 3,654,925 | 4/1972 | Holderith . |
| 3,771,965 | 11/1973 | Grams . |
| 3,826,260 | 7/1974 | Killinger . |
| 3,872,867 | 3/1975 | Killinger . |
| 3,983,037 | 9/1976 | Lee et al. . |
| 4,022,375 | 5/1977 | Suovaniemi et al. ................................. 494/16 |
| 4,030,663 | 6/1977 | Conn et al. . |
| 4,828,716 | 5/1989 | McEwen et al. . |
| 4,853,137 | 8/1989 | Ersson . |
| 5,037,549 | 8/1991 | Ballies . |
| 5,096,573 | 3/1992 | Bermudez . |
| 5,137,693 | 8/1992 | Mawhirt . |
| 5,393,674 | 2/1995 | Levine et al. . |
| 5,445,631 | 8/1995 | Uchida . |
| 5,653,686 | 8/1997 | Coulter et al. . |

OTHER PUBLICATIONS

Automated Blood–Sample Handling in the Clinical Laboratory, Clinical Chemistry, 36, 1551 (1990).

*Primary Examiner*—Charles E. Cooley
*Attorney, Agent, or Firm*—Mark M. Friedman

[57] ABSTRACT

Red cells are separated from plasma or serum of whole blood by arranging an evacuated tube sealed by a self-sealing stopper above and preferably coaxial with a tube containing a blood sample and sealed by a self-sealing stopper. A hollow double ended needle is held by a fixture and is disposed between and coaxial with the tubes and the tubes are placed in the fixture in a vertical position in a centrifuge and rotated about and spaced from an axis parallel to the axis of the tubes and needle. After the red cells are separated from the serum and/or plasma the tubes are pushed toward one another so that the needle penetrates both stoppers and the serum and/or plasma is drawn into the upper tube. The tubes and needle are separated while still being rotated so that the whole blood components are separated as required.

11 Claims, 5 Drawing Sheets

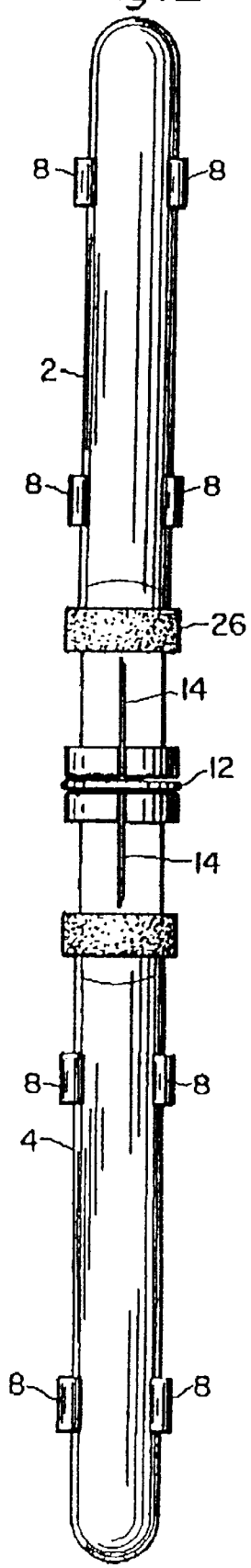
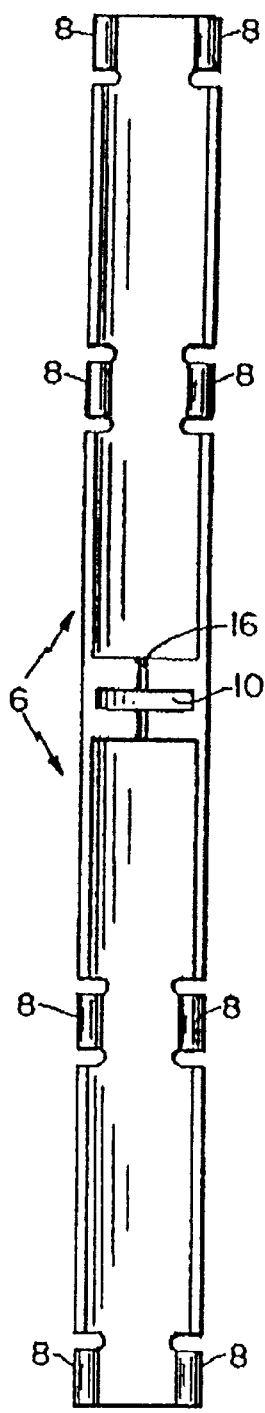
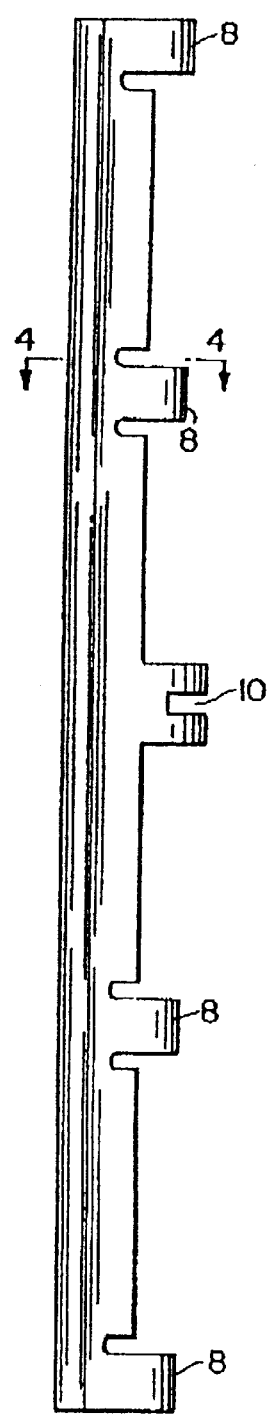
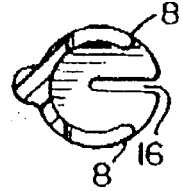

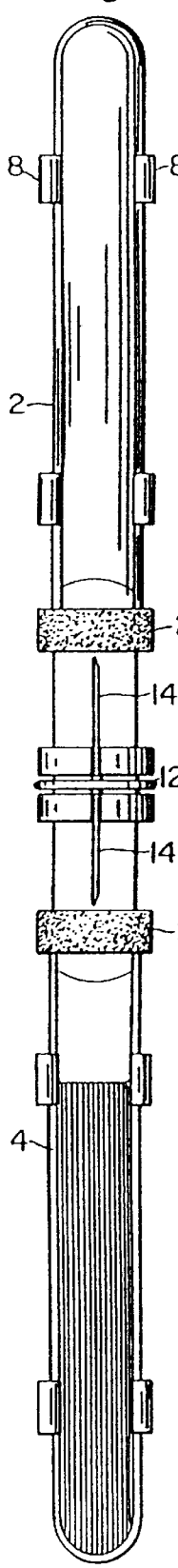
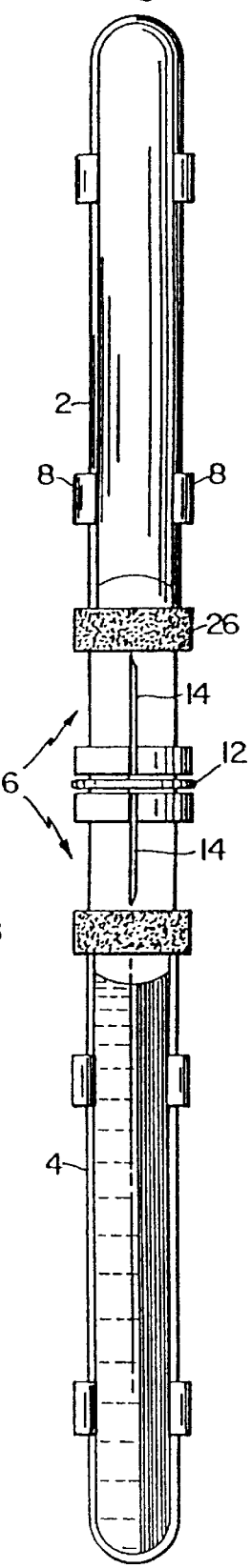
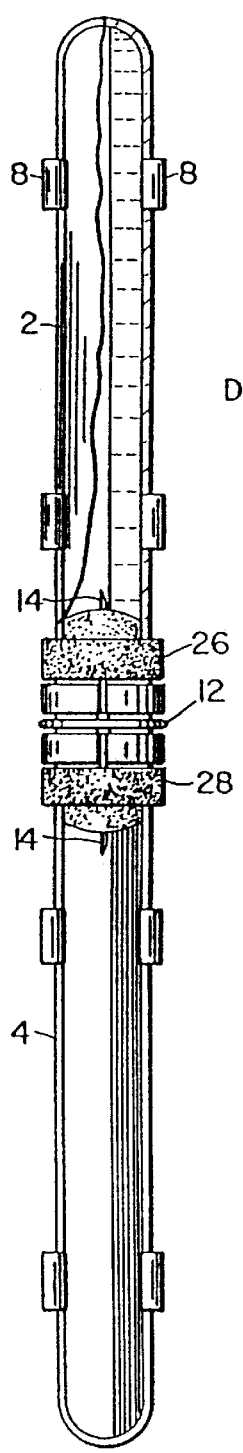
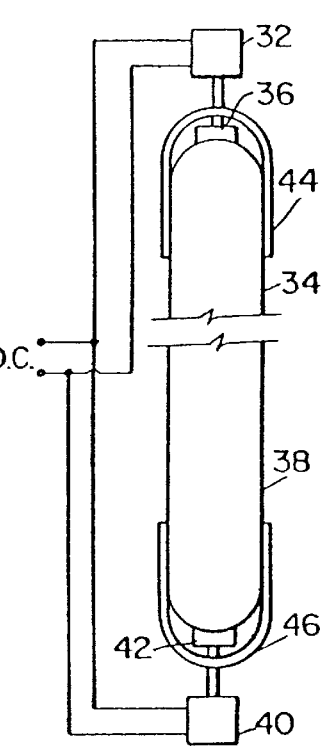

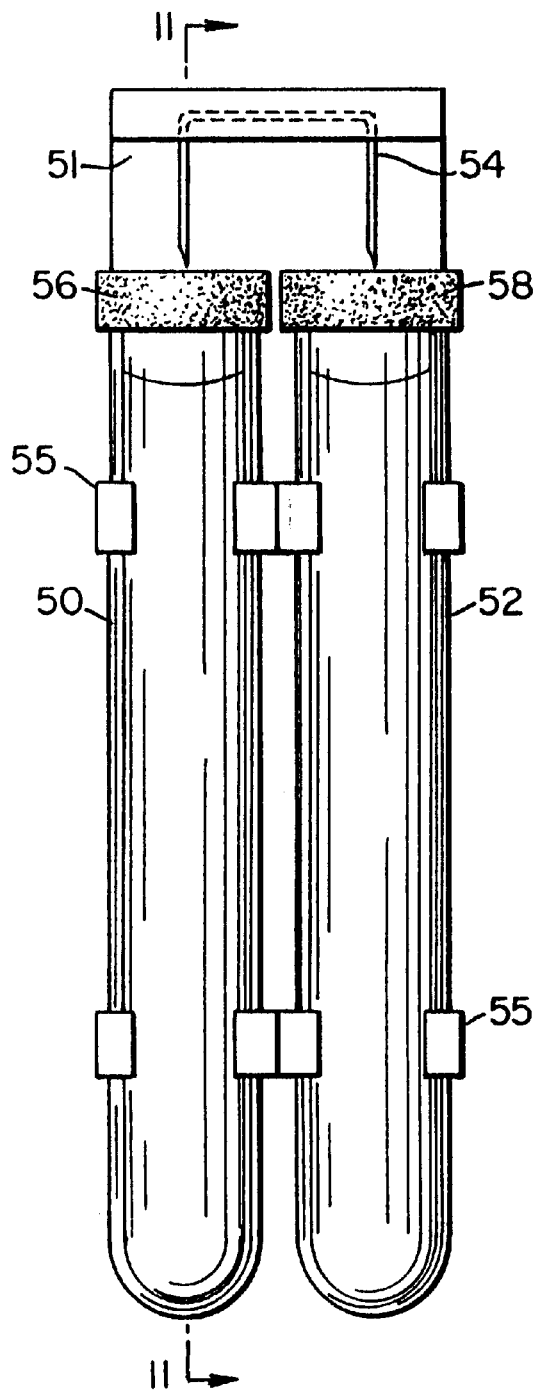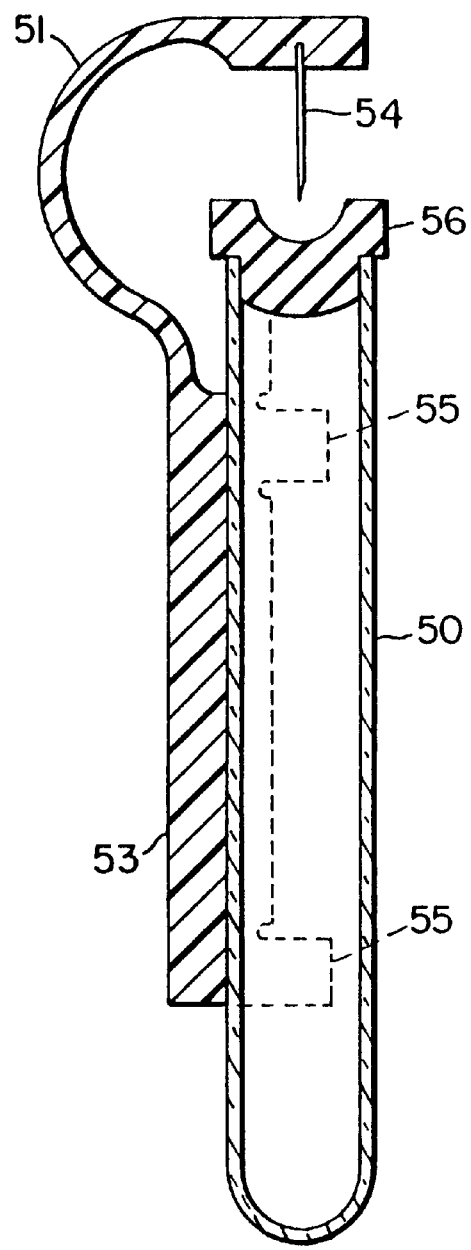

US 6,132,353

APPARATUS AND METHOD FOR SEPARATING PLASMA OR SERUM FROM THE RED CELLS OF A BLOOD SAMPLE

CROSS-REFERENCE TO RELATED APPLICATIONS

This application is a continuation-in-part of U.S. application Ser. No. 08/734,235 filed Oct. 21, 1996 for APPARATUS AND METHOD FOR SEPARATING PLASMA OR SERUM FROM THE RED CELLS WITH A BLOOD SAMPLE, now abandoned.

STATEMENT REGARDING FEDERALLY SPONSORED RESEARCH AND DEVELOPMENT

Not Applicable

FIELD OF THE INVENTION

The present invention relates to separation of plasma or serum from the red cells of a blood sample and more particularly to an apparatus and method for rapidly achieving such separation.

BACKGROUND OF THE INVENTION

In current practice plasma or serum is typically separated from the red blood cells of a blood sample by placing whole liquid or clotted blood respectively, in a tube, placing the tube in a swinging bucket type centrifuge which upon activation rotates rapidly and causes the tube to acquire a horizontal position. The red cells being heavier than the plasma or serum migrate to the end of the tube furthest from the center of rotation thus producing separation of the various components of the sample.

The above procedure is time consuming requiring extended periods of centrifuging to achieve the desired results because of the long migration path of the red cells.

U.S. Pat. No. 3,190,547 to J. J. Shanley discloses in FIGS. 10–13 a centrifuge wherein bottles are located below evacuated plasma receivers. The combination of each bottle and receiver is rotated together with other such combinations about an axis parallel to the axis of each combination, which axis passes through a bottle and receiver. In consequence red cells migrate upon rotation of the bottles about such axis toward the outer walls of the sample bottles. Upon completion of centrifuging the sample bottle and plasma receivers are connected through hollow needles situated in self-sealing stoppers in each member of the combination. The plasma is drawn into the plasma receivers which are then spun at a higher than previous rotational velocity separately from the now stationary specimen bottles to produce further separation of the materials drawn therein.

The mechanism is very complex requiring two separately driven rotating shafts, two different hollow needles to affect interconnection of the bottle and the receiver, rectangular shaped or other non-cylindrical specimen bottles to ensure that the bottles do not rotate about their own axes. This procedure further requires proper registration of the needle with the sample bottle. To provide proper alignment with the various strata in the specimen bottle, a readily movable self-sealing stopper in the specimen bottle is employed to assist in the search for the strata of the material desired. This procedure may require opening of the specimen bottle to locate the strata interface thus compromising the sterility of the specimen and possibly endangering the workers.

OBJECTS OF THE INVENTION

It is an object of the present invention to greatly shorten the time required to separate the components of either anticoagulated and/or clotted blood samples.

It is another object of the present invention to produce separation of the red blood cells from other components of whole blood in a system in which the plasma or serum at the end of the process is disposed in a separate container from the red cells.

Still another object of the present invention is to automatically separate serum or plasma into a different container from red blood cells from which the serum or plasma has been extracted.

Still another object of the present invention is to provide a quite simple assemblage for application to a centrifuge, the assemblage comprised of two test tubes, with self-sealing stoppers, a two ended hollow needle and a universal fixture to hold the tubes and needles in proper coaxial registration.

Yet another object of the present intention is to provide an apparatus for rapidly separating plasma or serum from blood samples by an assembly having a fixed structure of small size employing standard test tubes of the type employed by medical and paramedical personnel to withdraw blood from a patient.

It is another object of the invention to provide a fixture for holding the assemblage in registration, the fixtures all having a universal interface for registration with a centrifuge designed for such purpose and having a second interface that varies only with the dimensions of the test tubes. Thus loading and unloading of the centrifuge is simple and lends itself to automated input to and output from the machine. Also such arrangement increases safety by reducing the contact of laboratory personnel with the equipment and the danger of contact with potentially contaminated blood.

BRIEF SUMMARY OF THE PRESENT INVENTION

The preferred embodiment of the present invention is comprised of a spinning drum, which spins a plurality of pairs of head-to-head tubes held coaxially of one another and located around a vertical axis parallel to and spaced from the longitudinal center line of the tubes. Each pair of tubes is arranged head to head in which a primary tube contains blood while a collection tube is under vacuum and is empty. The primary or sample tube is located below the collection tube.

When the drum rotates, the red cells migrate a quite short distance to one side of the primary or sample tube. The separation time is quite short because of the shorter separating distance compared to the present method in which the cells are driven to the bottom of a tube, or in the Shanley patent to the walls of a 500 ml bottle. There is less chance of damage to the red cells due to the smaller radial pressure required. The use of small vessels such as test tubes has the advantage of more uniform pressure across the tube and thus a calculated maximum force may be employed without fear of damage to the specimens. Large vessels do not permit uniform pressures across the vessels so that lower average forces must be employed to insure that excessive pressure is not developed in the sample. Also in larger vessels separation may not be uniform as a result of non-uniform pressure.

The two tubes of each pair, in accordance with the present invention, the sample and collection tubes, are connected during the interval the drum is rotating by a single two sided hollow needle. The needle is introduced into the center of each of the tubes through self-sealing stoppers substantially simultaneously. The plasma flows into the collection tube by reason of the partial vacuum in the collection tube and the pressure developed by the centrifuging action in the primary tube. It is to be noted that in humans the red cell and other non-plasma or serum volume of blood represents about 44% in males and 41% in females. The sample tube is usually not completely filled, 80% to 90% being the usual. At 90% with 44% red cells, only about 40% of the tube contains red cells thus providing a reasonable margin of safety. With a 41% red cell sample only 37% of the tube is filled with red cells. Thus the red cells and other non-serum or plasma materials are not near the center of the sample tube as a result of centrifuging and the two ended needle may be located along the center line of the tubes. Red cells are not available to the needle and therefore will not pass into the empty collecting tube. This feature provides a plasma or serum containing tube at the end of centrifuging suitable for use in the analytical determinations without any further serum or plasma transfer steps required. Further it is not necessary to perform any function that can compromise the sterility of the sample.

Further, in accordance with the preferred embodiment, there is a fixture which holds the two tubes facing each other and a hollow needle having two sharp ends in between. The tubes must have self-sealing stoppers or caps so that the blood flows only through the needle and does not spin out of the tubes. The tubes and needle can be snapped on or off the fixture manually or automatically. Further, the fixture with the tubes can be loaded or unloaded manually or automatically onto the drum. After the separation is completed and while the centrifuge is still spinning the two tubes are forced to slide towards each other so that the needle penetrates both stoppers allowing plasma to flow from the primary to the collection tube. The needle is preferably held by a disc that is snugly received by the fixture and may be made integral with the fixture. In all cases the needle should be a disposable item.

The collection tube can be labeled after it is placed in the fixture by any of several well known technologies such as laser printing directly onto the glass or plastic of the collection tube or on a sticky back label so that the collection tube label matches exactly a bar code or other code on a readable label previously applied to the sample tube. This approach assure positive specimen identification and replaces a step currently performed by other less dependable methods in which mislabeling of the collection tube can occur. Both tubes can be pre-labeled and the labeling verified upon insertion into the centrifuge by a computer or other suitable means.

Furthermore, the drum is provided with a plurality of bays, each of which can contain a fixture with tubes. The bay is directed inwardly opposite to the direction of rotation so that inertia forces the fixture into its designated position. The bays are designed, however, such that it is easy to replace the fixtures with the tubes by an external device that loads and unloads the centrifuge. The fixture can accommodate tubes of different sizes and different fixtures may be employed for different size tubes. The interface with the centrifuge remains the same.

Regardless of the nature of the sample, the above described assemblage is fully functional. If the sample has been drawn into a tube with an anticoagulant, it remains a liquid and the distribution is as stated above. If the sample is drawn into a tube without an anticoagulant the blood clotting proteins will polymerize about the blood platelets which had previously agglutinated, and after a predetermined time say, for instance, 10 minutes, will form a gelatinous mass or blood clot. This mass is usually formed directly in the sample tube and centrifuged. Since the distribution of red cells and related material in the clot and the serum is essentially the same as that of the red cells and plasma in a liquid sample, the assemblage remains the same. Thus regardless of the nature of the specimen or sample, the simple arrangement described above is completely suitable for the task.

As will become apparent subsequently the entire system is designed around the disposables; two test tubes, a needle and a couple of stoppers. The fixture may also be disposable. The geometry is slender, easily handled and provides short sample separation times. Further the system is designed for automation particularly since assembly of the tubes, fixture, etc. is quite simple.

The above and other features, objects and advantages of the present invention, together with the best means contemplated by the inventors for carrying out the invention will become more apparent from reading the following description of a preferred embodiment and perusing the associated drawings in which:

BRIEF DESCRIPTION OF THE DRAWINGS

FIG. 1 is a front view of the assembled containers, the needle and the fixture for holding the assembled containers;

FIG. 2 is a front view of the fixture;

FIG. 3 is a side view of the fixture;

FIG. 4 is a detail taken along section line 4—4 of FIG. 3;

FIG. 6 illustrates the tubes, fixture and needle with lower tube filled with whole blood;

FIG. 7 illustrates the separation of the blood components as a result of centrifuging;

FIG. 8 illustrates the position of the tubes upon transfer of materials;

FIG. 9 is a view of one of the chambers for holding a fixture, container and needle illustrating the location of the solenoids for bringing the containers together and for separating them;

FIG. 10 illustrates a different arrangement of the sample and collection tubes;

FIG. 11 is a side view of the apparatus of FIG. 10; and

DETAILED DESCRIPTION OF THE INVENTION

Figure 5:
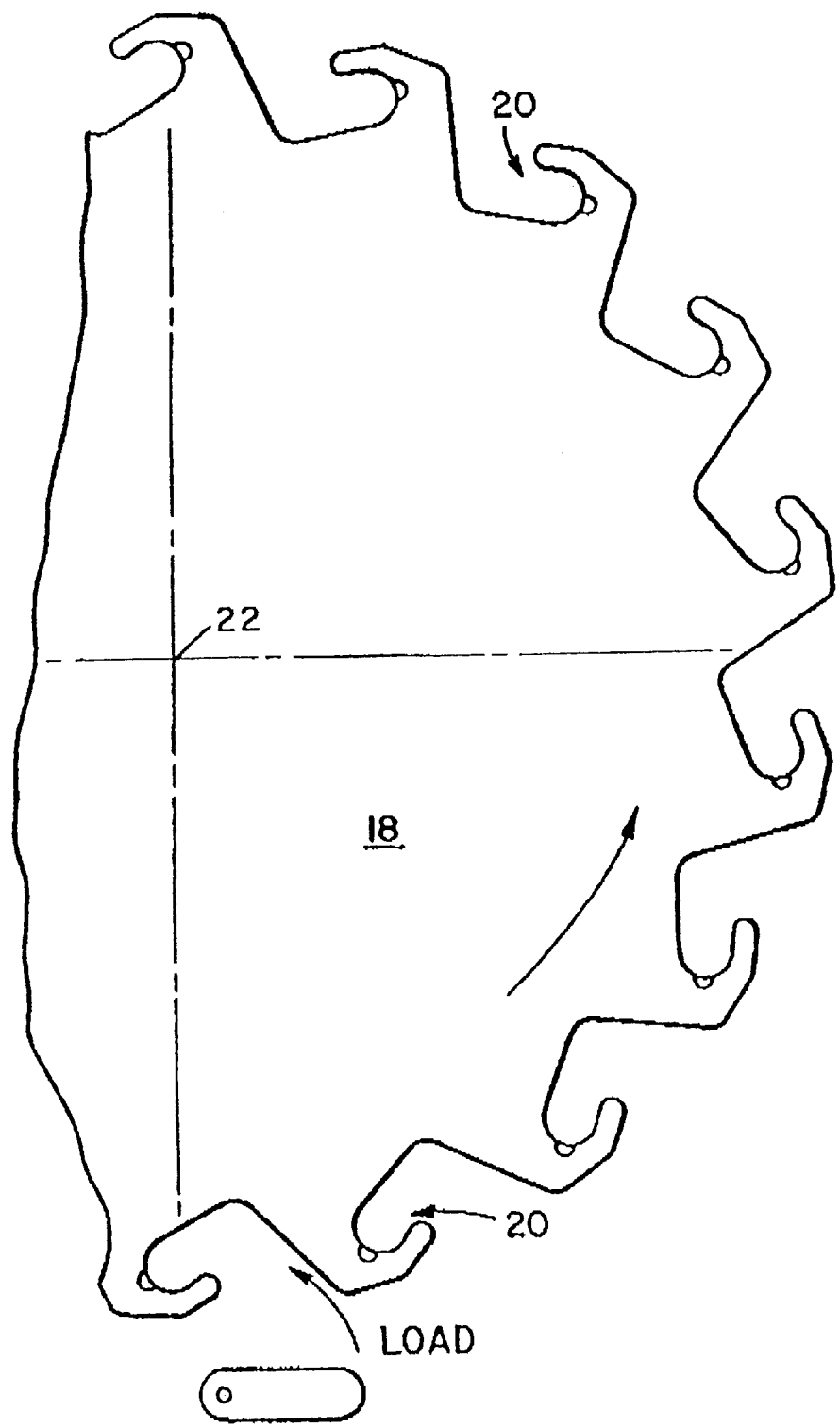
FIG. 5 is a top view of the part of the centrifuge for holding the fixtures, containers and needles.

Referring specifically to FIGS. 1–4 of the accompanying drawings, two tubes 2 and 4 are held head-to-head in a fixture 6. The fixture has several sets of opposed spring fingers 8 for grasping the tubes when inserted into the fixture 6. Two sets of spring fingers are illustrated for each tube. Located in the center of the fixture is a slot 10 for receiving a slotted needle holder 12. A needle 14 may be integral with fixture 6. The needle holder is insertable into horizontal slot 10 of FIGS. 1–3 with the needle seated in vertical channels 16, FIG. 2. Thus the needle is firmly held in place, FIG. 1. The position of the needle 14 and needle holder 12 is clearly illustrated in FIG. 1. FIG. 4 illustrates a slot 17 through which the needle passes as the needle holder 12 is inserted into slot 10. The needle, needle holder and fixture may be cast as a unit.

The assemblage is held together by the fixture 6 a slim simple device made of a spring type material so that all elements of the assemblage are firmly held in place. The stoppers and the test tubes are normally available in the industry and together with the needle and possibly the fixture are considered disposable. As previously indicated the structure is such that the needle may be and preferably is held along the center line of the tubes. The bevel of the needle is oriented away from the red cells. The fixture's spring fingers at one of its ends may be of a size to accommodate a tube of a different dimension from the fingers at its other end. Also the length of the needle may vary to accommodate tubes of different lengths and may fill the space between the stoppers.

Referring to FIG. 5, there is illustrated a region of the fixture holders 18 of a centrifuge. A fixture, such as fixture 6 of FIGS. 1–3, is insertable into each receiver 20 of a centrifuge having a plurality of receivers 20. The fixtures are situated with the center line of the tubes and needle parallel to spin center 22 of the centrifuge. The spin rate may be anywhere from 60 rps to 120 rps.

The fixture 6 is of such structure as to interface with the centrifuge regardless of the sizes of the tubes. As can be seen in FIG. 5 the receivers 20 of the centrifuge may be or are identical and are provided with a notch 21 for receiving a projection 23 on the fixture 6, see FIG. 4, to stabilize the position of the structure in the receiver 20.

Both coagulated and uncoagulated blood may be processed at the same time so as to produce serum in the one instance and plasma in the other. The centrifuge as indicated above has numerous pockets and the sample in each pocket has no relationship to the samples in any of the other pockets so that both types of materials can be centrifuged concurrently. Thus plasma and/or serum can be the end product or products.

Reference is now made to FIGS. 6–8. In FIG. 6 tubes 2 and 4 are fully separated (extended) with liquid or coagulated whole blood in sample or lower tube 4. FIG. 7 illustrates the tubes after centrifuging with the red cells compacted against the region of the tube wall remote from the center of rotation of the centrifuge. The red cells constitute only about 37% to a maximum of about 44% in the latter case if the tube is fully filled. Thus the center 25 of the lower tube 4 rarely if ever contains red cells as a result of centrifuging for a time necessary to effect complete separation, one minute or less in a standard size tube.

Referring now to FIG. 8 of the accompanying drawings, the tubes 2 and 4 have been pushed together causing needle 14 to penetrate self-sealing stoppers 26 and 28 and establish communication between tubes 2 and 4. The vacuum in tube 2 and the pressure created by centrifuging in the sample tube causes the plasma or serum, to be transferred to the upper tube 2. Thereafter the tubes may be separated while the centrifuge is still rotating, the stoppers 26 and 28 sealing their respective tubes. The centrifuge may now be stopped, the fixture(s) with tubes may be removed and the tubes processed separately thereafter. If the material remaining in the sample tube is not to be used the sample tube may also be discarded.

Referring to FIG. 9, a solenoid 32 is connected to a cap 44 that is disposed about the top of upper tube 34 of an array employed in the present invention. A plate 36 presses on the top of the tube 34 to force it down to cause the upper tube 34 to move toward lower tube 38. Concurrently solenoid 40 is energized to move lower tube 38 upward whereby the tubes 34 and 38 assume the position of FIG. 6 hereof.

On the end of each solenoid shaft is an elastic sleeve with the plate 36 of solenoid 32 at the upper end of the structure as viewed in FIG. 9. There is a corresponding plate 42 of solenoid 40 disposed inside of sleeve 46. Upon reversal of polarity to the solenoids, the needle is withdrawn from the tubes.

It is not necessary that the needle be coaxial with the tubes. The needle may be off center away from the side of the tubes in which the red cells are collected to further insure in those rare instances that red cells may be near the center so that none of the red cells are drawn into the upper tube. Such an occurrence is quite uncommon if not essentially impossible. Note the level of the needle away from the red cells. Further, location of the collection tube above the sample tube permits gravity to assist in the separation of the heavier red cells from the plasma and serum. It is not necessary that the two tubes be of the same length or diameter. A fixture may be provided that can accommodate different size tubes or different fixtures may be provided for each different combination of test tubes or a test tube and plastic tubing. It is not necessary that the upper tube be a test tube. It can be a hose (plastic tubing) connected, for instance, to a vacuum pump that is energized at approximately the same time as the solenoid to produce puncture of the self-sealing stopper by the needle. The hose discharges into a suitable container.

Figure 12:
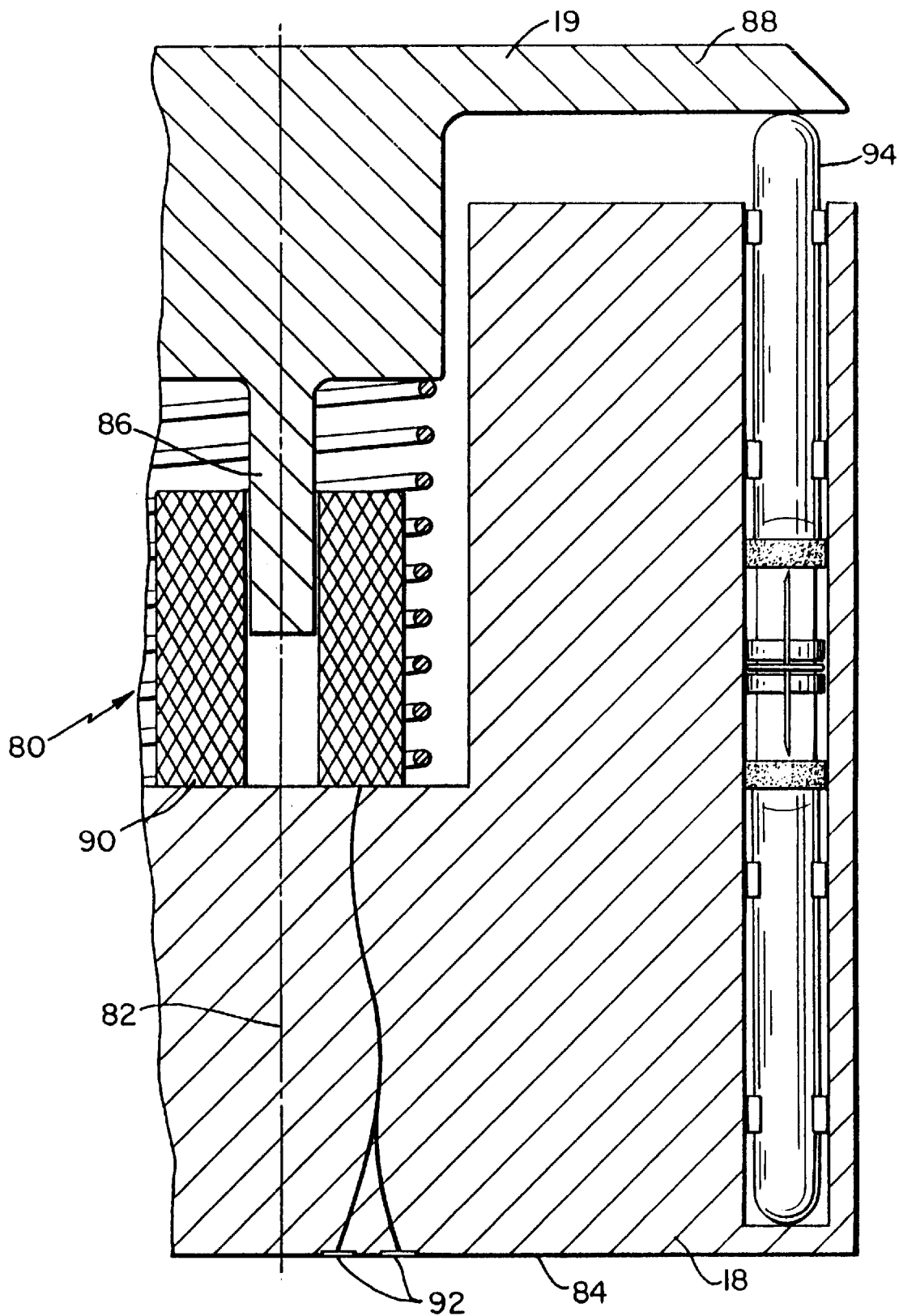
FIG. 12 illustrates a structure for causing all of the needles of various structures in the pockets of a centrifuge to pierce their associated tube structures concurrently.

Referring now to FIG. 10 of the accompanying drawings, there is illustrated an arrangement of standard sample and receiver tubes 50 and 52, respectively, arranged side by side. The tubes 50 and 52 are held by spring fingers 55 of a fixture 53 that is insertable into pockets of a centrifuge. A U-shaped needle 54 is positioned above stoppers 56 and 58 of both tubes and is attached to a leaf spring 51 so as to be poised above the stoppers. Depression of the springs, as by the apparatus of FIG. 12, connects the tubes 50 and 52.

It is apparent that at no time in the procedure is the sample, the serum or the plasma exposed to the air and thus its contents cannot reach the external environment. The risk is eliminated to blood workers of exposure to disease causing microorganisms in blood in this step that otherwise could occur upon removal of the stopper from either tube. Removal of a stopper is accompanied by formation of droplets or aerosol from liquid blood or clots during manual transfer of plasma or serum to a secondary collection tube.

The arrangements of FIG. 9 is acceptable for a single pocket arrangement but would be awkward for a multiple pocket arrangement. The structure of FIG. 12, however, is suitable for multiple pockets. In this structure a solenoid 80 is symmetrical with respect to axis 82 of the centrifuge 84. Armature 86 of the solenoid 80 provides across its top a plate 88 that lies about all of the pockets of the centrifuge. Coil 90 of the solenoid 80 is connected through slip rings 92 located on a surface of the centrifuge.

The armature 86 and its plate 88 are biased upwardly as viewed in FIG. 11 but upon energization of the solenoid the armature is retracted into the coil 90 and the plate presses down on receiver tubes 94 of tube and fixture structures located in the pockets of the centrifuge. The sleeve arrangement of FIG. 9 may be employed to extract the needle from the tubes.

The geometry of this system or assemblage is remarkably simple, the fixture 6 is responsible for and does at all times maintain the assemblage. The assemblage can handle both coagulated and uncoagulated blood in the centrifuge at the same time. The structure is designed around inexpensive disposables. Further because of its slim design it can produce separation of red cells, etc. from serum or plasma in a matter of approximately one minute or less at speeds of 60 to 120 rps. In still another arrangement the collection tube may be integral with the fixture.

Once given the above disclosure, many other features, modifications and improvements will become apparent to the skilled artisan. Such features, modifications and improvements are, therefore, considered to be a part of this invention, the scope of which is to be determined by the following claims.

We claim:

1. A structure composed of several components comprising a plurality of sample holders each having a first axis,
a centrifuge having a member rotatable at high speed about a second axis parallel to said first axes,
said member having a plurality of pockets displaced from said second axis with each pocket to receive a different sample holder, a plurality of specimen receivers paired on a one for one basis with said sample holders and coaxial therewith, a hollow needle with two sharp ends, self sealing stoppers in each said sample holder and each said specimen receiver, means holding a different needle in coaxial relation with the axis of each of said paired holders and receivers, and means holding each of said paired holders and receivers as a unit in a different one of said pockets.

2. A structure composed of several components according to claim 1 further comprising, means for bringing said sample holders and specimen receivers toward one another sufficiently to cause the needle to penetrate said stoppers and enter said specimen receivers and sample holders, said means for bringing including means for subsequently separating said sample holders and said specimen receivers.

3. A structure according to claim 2, further comprising said means for bringing moves only one of said sample holders so as to bring said sample holders and receivers close together to cause the ends of the needle to penetrate said stoppers.

4. A structure composed of several components according to claim 1 further comprising an outwardly extending projection from each said holding means, each said pocket having means to engage said projection to maintain orientation of said sample holders and said receivers in said pockets.

5. A structure composed of several elements comprising first and second hollow cylindrical members, each having one end closed and a self-sealing stopper closing the other end, first means holding said first and second cylindrical members colinearly, a hollow needle sharp at both ends, the sharp ends of said needle disposed adjacent the stoppers of said cylindrical members and located substantially along the axes of the cylindrical members, a centrifuge having a spin axis parallel to the axes of the hollow members, said centrifuge having a plurality of pockets along its outer circumference, said pockets each for receiving a pair of colinearly related cylindrical members, said first means and said needle, and means on said centrifuge for concurrently causing said needles to pierce their respective stoppers.

6. A structure according to claim 5 wherein said first means is a unitary structure holding said cylindrical members and needle coaxially.

7. A structure composed of several components comprising a plurality of sample holders each having a first axis, a centrifuge having a member rotatable at high speed about a second axis parallel to said first axes, said member having a plurality of pockets displaced from said second axis with each for receiving a different sample holder, a plurality of specimen receivers paired on a one for one basis with said sample holders and having an axis parallel to said first and second axis, a hollow needle with two sharp ends, self sealing stoppers in each of said holders and said receivers, means holding a different needle in coaxial relation with the axes of each said holders and receivers, and means holding each of said pair of holders and receivers in different ones of said pockets.

8. A tube and needle arrangement employed to separate constituents of a fluid comprising, first and second tubes, said first tube having a central axis for receiving a fluid to be separated into its various components, a self sealing stopper closing one end of said first tube, said second tube having a central axis for receiving a specified component of the fluid in the first tube, a self sealing stopper closing one end of the second tube, said second tube having a partial vacuum therein, a single hollow needle having two sharp ends located along the central axes of the tubes and the of the self sealing stoppers, a unitary means holding said first and second tubes and said needle in coaxial alignment between said tubes with said sharp ends each facing a different one of said self sealing stoppers, means for rapidly rotating the tubes about an axis generally parallel to the axes of the hollow tubes to separate the fluid into its various components, means for causing the ends of the needle to penetrate said stoppers along their central area and enter the interior of the tubes, and means for withdrawing the ends of the needle from the tubes while the means for rapidly rotating remains in rapid rotation.

9. A tube and needle arrangement according to claim 8 wherein the interior of each of said tubes is symmetrical with respect to its axis.

10. A structure comprising a sample container having an axis and an interior wall symmetrical with respect to said axis, a receiver container having an interior wall and an axis symmetrical with respect to said wall, both said containers closed by self-sealing stoppers, a generally U-shaped hollow needle sharp at both ends and having two legs and a base, means for holding said containers with their axes parallel to one another and with said needle disposed above said containers with the ends of the needle each aligned with a different one of said axes, and means for depressing said needle to cause the ends of the needle to penetrate the stoppers and enter the containers.

11. A method of separating a fluid sample into its constituent components comprising mounting two containers having cylindrical interiors side-by-side in a vertical position, the containers having a closed end and an open end, closing the open ends of the containers with self-sealing stoppers, mounting a two ended hollow needle having sharp ends above the self-sealing stoppers, spinning the containers about a vertical axis remote from said containers, and after a predetermined time forcing the ends of the needle into the containers through the self-sealing stoppers.

* * * * *